(12) United States Patent
Yu et al.

(10) Patent No.: US 10,131,956 B2
(45) Date of Patent: Nov. 20, 2018

(54) MARKER USED FOR DETECTION OF COLON CANCER, AND APPLICATION THEREOF

(71) Applicant: SHENZHEN GENEBIOHEALTH CO. LTD., Shenzhen (CN)

(72) Inventors: Haoyang Yu, Shenzhen (CN); Mianqiao Chen, Shenzhen (CN)

(73) Assignee: SHENZHEN GENEBIOHEALTH CO. LTD., Shenzhen (CN)

( * ) Notice: Subject to any disclaimer, the term of this patent is extended or adjusted under 35 U.S.C. 154(b) by 0 days.

(21) Appl. No.: 15/503,790

(22) PCT Filed: Aug. 14, 2015

(86) PCT No.: PCT/CN2015/086956
§ 371 (c)(1),
(2) Date: Feb. 14, 2017

(87) PCT Pub. No.: WO2016/023515
PCT Pub. Date: Feb. 18, 2016

(65) Prior Publication Data
US 2017/0356050 A1    Dec. 14, 2017

(30) Foreign Application Priority Data
Aug. 15, 2014    (CN) .......................... 2014 1 0403598

(51) Int. Cl.
*C12Q 1/68*    (2018.01)
*C12Q 1/6886*    (2018.01)

(52) U.S. Cl.
CPC ............. *C12Q 1/6886* (2013.01); *C12Q 1/68* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2011/0143360 A1* 6/2011 Kuroda ................ C12Q 1/6886
435/6.14

FOREIGN PATENT DOCUMENTS

| CN | 101988060 A | 3/2011 |
|---|---|---|
| CN | 102421916 A | 4/2012 |
| CN | 102933719 A | 2/2013 |
| CN | 102985564 A | 3/2013 |
| CN | 103080334 A | 5/2013 |
| CN | 103173448 A | 6/2013 |
| CN | 103180461 A | 6/2013 |
| CN | 103667516 A | 3/2014 |
| CN | 104195238 A | 12/2014 |

OTHER PUBLICATIONS

Qu, Changmin et al., "MiRNA expression profiling of rectal adenocarcinoma", World Chinese Journal of Digestology, Jun. 8, 2012, pp. 1407-1414, vol. 20. No. 16, Beijing.

* cited by examiner

*Primary Examiner* — Katherine D Salmon
(74) *Attorney, Agent, or Firm* — IPro, PLLC; Na Xu; Qian Gu

(57) ABSTRACT

The present invention provides a marker used for detecting colon cancer, and also provides application of said marker in the detection of colon cancer, as well as an associated kit and detection method.

13 Claims, 7 Drawing Sheets
Specification includes a Sequence Listing.

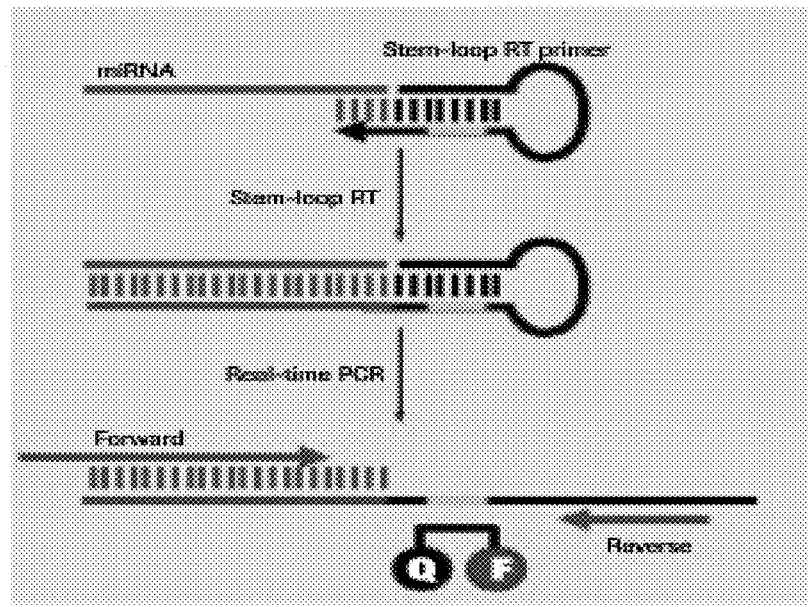
Figure 1  A Schematic Diagram of Probe Detection Method
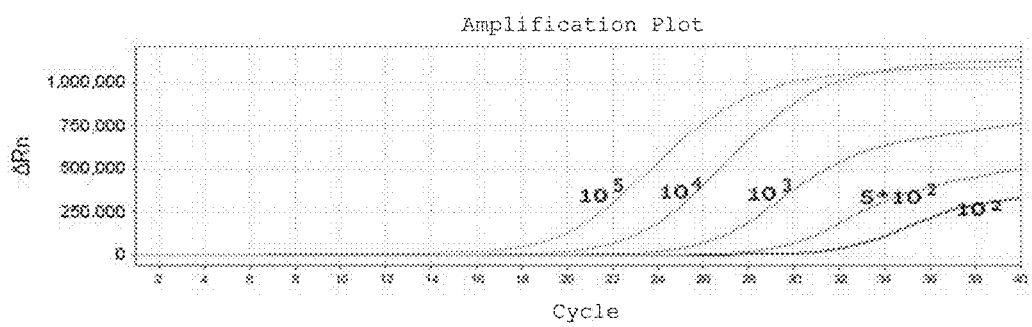
Figure 2 Detection Limit for miRNA-19
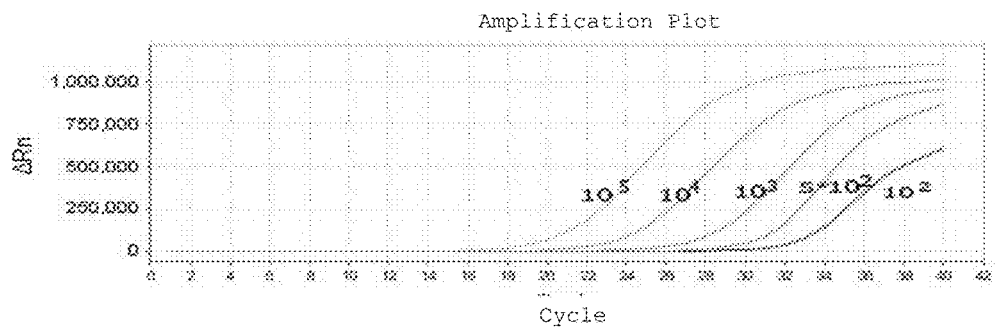
Figure 3 Detection Limit for miRNA-135b

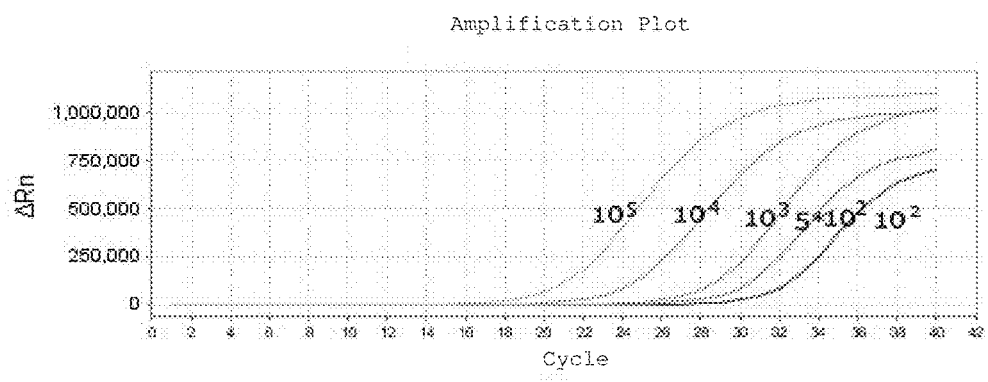
Figure 4 Detection Limit for miRNA-18a
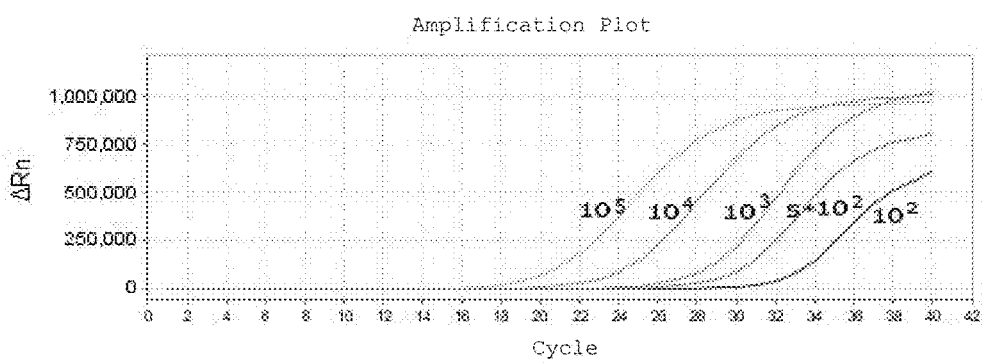
Figure 5 Detection Limit for miRNA-221
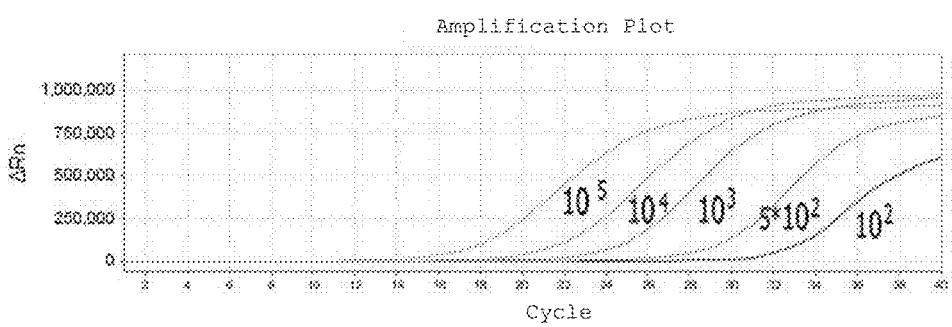
Figure 6 Detection Limit for miRNA-92a

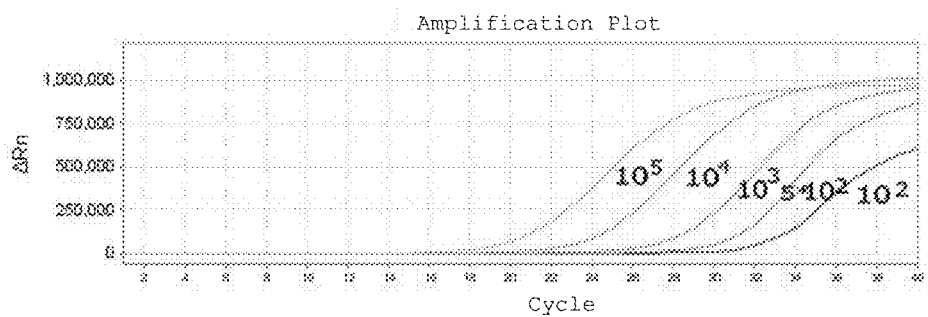
Figure 7 Detection Limit for miRNA-223
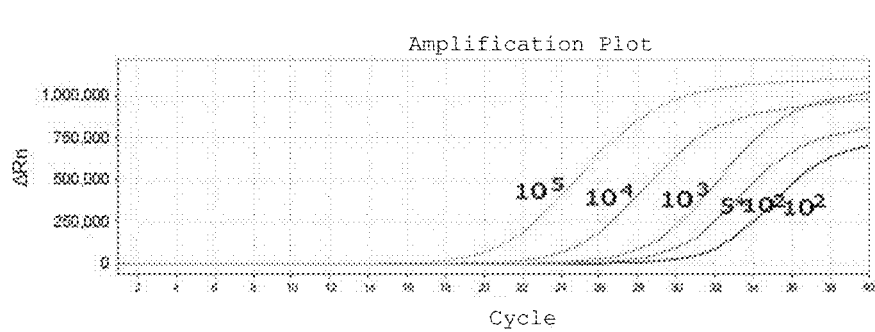
Figure 8 Detection Limit for miRNA-301a
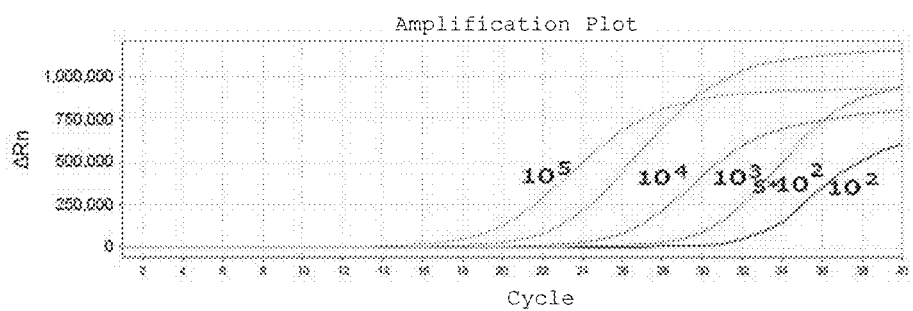
Figure 9 Detection Limit for COX2

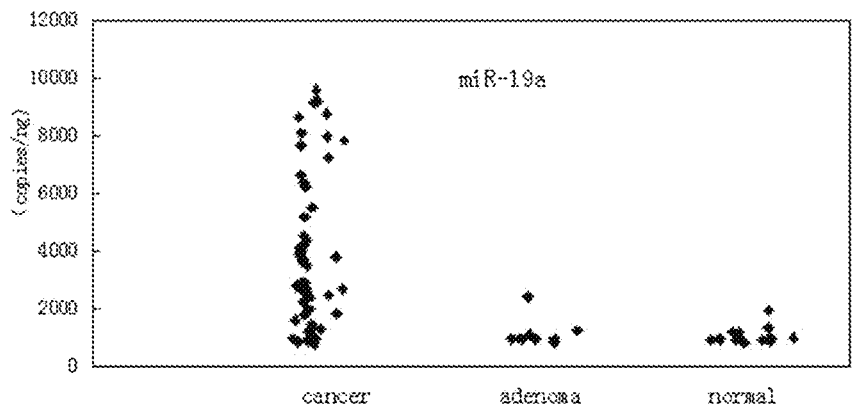
Figure 10 Expression Level of miRNA-19a
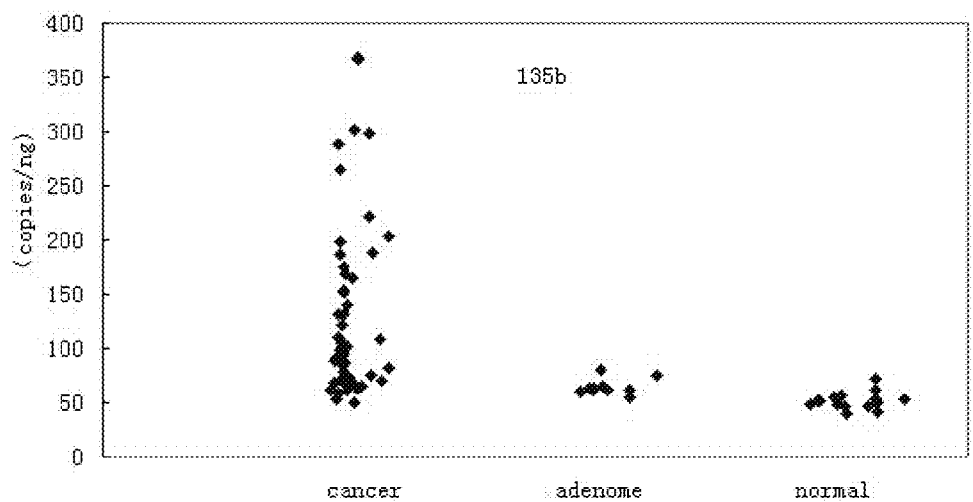
Figure 11 Expression Level of miRNA-135b

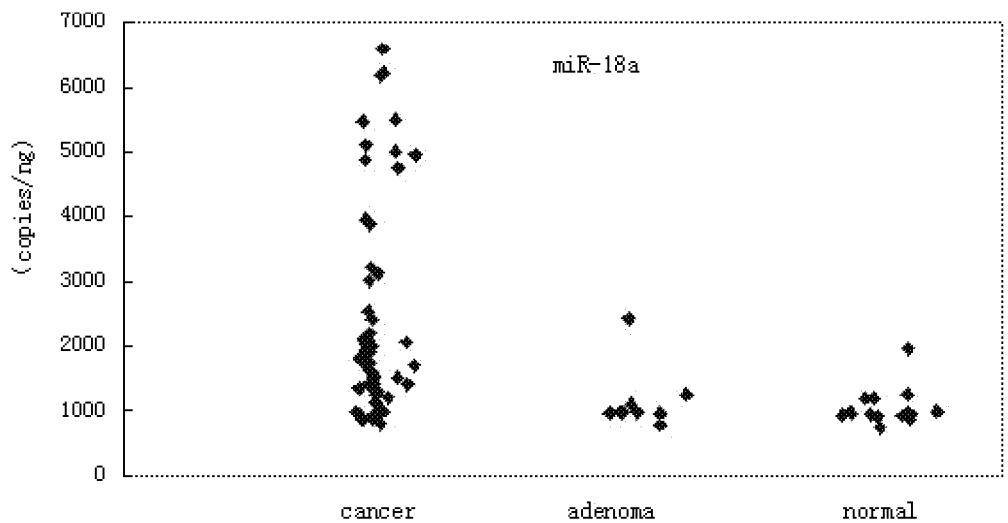
Figure 12 Expression Level of miRNA-18a
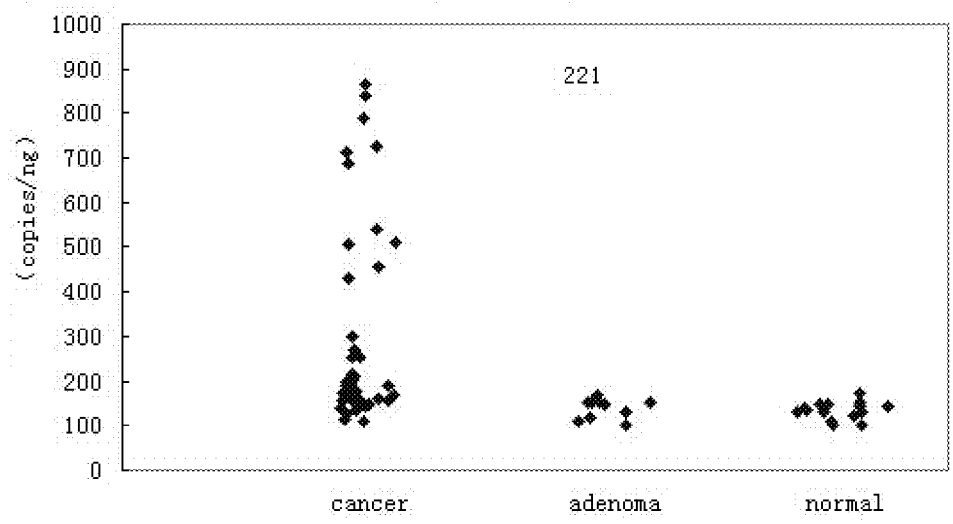
Figure 13 Expression Level of miRNA-221

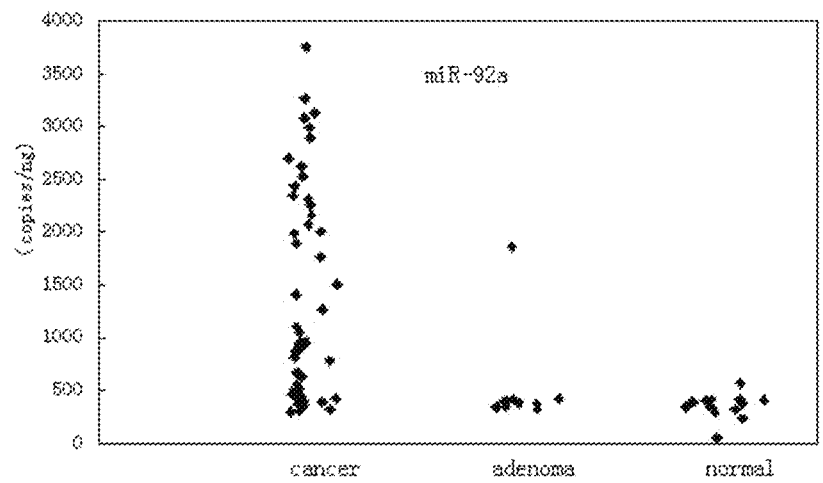
Figure 14 Expression Level of miRNA-92a
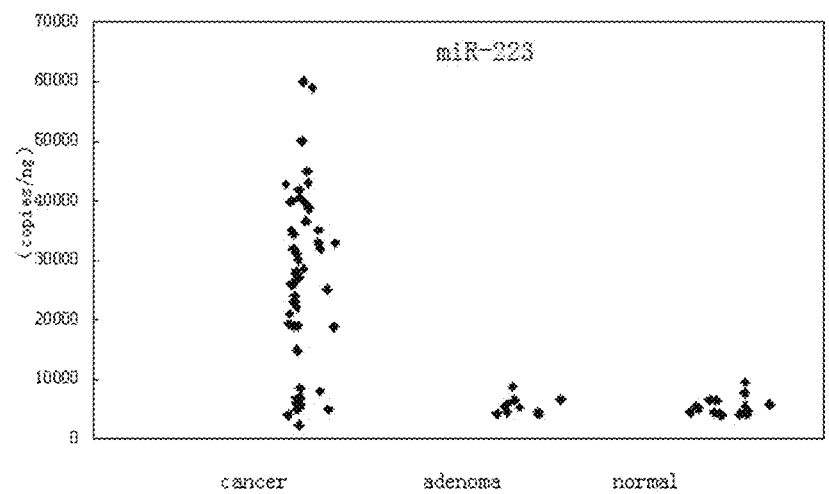
Figure 15 Expression Level of miRNA-223

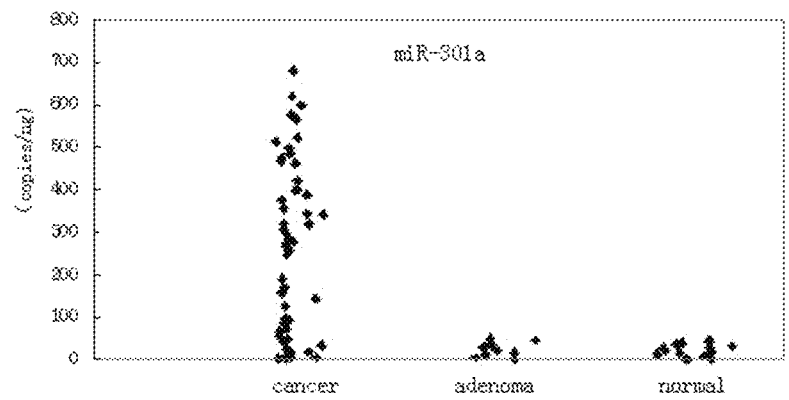
Figure 16 Expression Level of miRNA-301a
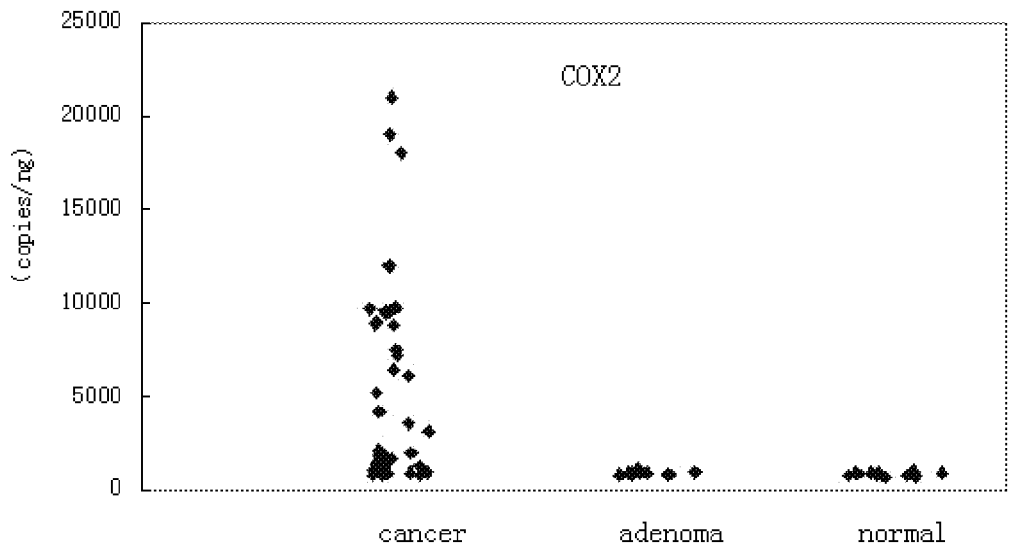
Figure 17 Expression Level of COX2

SEQUENCE LISTING

<160> NUMBER OF SEQ ID NOS: 27

<210> SEQ ID NO 1
<211> LENGTH: 21
<212> TYPE: RNA
<213> ORGANISM: Homo sapiens

<400> SEQUENCE: 1
uauugcacuu gucccggccu g                     21

<210> SEQ ID NO 2
<211> LENGTH: 23
<212> TYPE: RNA
<213> ORGANISM: Homo sapiens

<400> SEQUENCE: 2
uauggcuuuu cauuccuaug uga                   23

```
<210> SEQ ID NO 3
<211> LENGTH: 23
<212> TYPE: RNA
<213> ORGANISM: Homo sapiens

<400> SEQUENCE: 3
uaaggugcau cuagugcaga uag                                            23

<210> SEQ ID NO 4
<211> LENGTH: 23
<212> TYPE: RNA
<213> ORGANISM: Homo sapiens

<400> SEQUENCE: 4
agcuacauug ucugcugggu uuc                                            23

<210> SEQ ID NO 5
<211> LENGTH: 23
<212> TYPE: RNA
<213> ORGANISM: Homo sapiens

<400> SEQUENCE: 5
ugugcaaauc uaugcaaaac uga                                            23

<210> SEQ ID NO 6
<211> LENGTH: 22
<212> TYPE: RNA
<213> ORGANISM: Homo sapiens

<400> SEQUENCE: 6
ugucaguuug ucaaauaccc ca                                             22

<210> SEQ ID NO 7
<211> LENGTH: 23
<212> TYPE: RNA
<213> ORGANISM: Homo sapiens

<400> SEQUENCE: 7
cagugcaaua guauugucaa agc                                            23

<210> SEQ ID NO 8
<211> LENGTH: 133
<212> TYPE: DNA
<213> ORGANISM: Homo sapiens

<400> SEQUENCE: 8
cacttgacca gagcagagag atgaaatacc agtcttttaa tgagtatcgc aaacgttttc    60
tgctgaagcc ctatgaatct tttgaggaac ttacaggaga aaggaaatg gctgcagagt    120 tagaagcgct cta                                                      133

<210> SEQ ID NO 9
<211> LENGTH: 61
<212> TYPE: DNA
<213> ORGANISM: Artificial Sequence
<220> FEATURE:
<223> OTHER INFORMATION: Primer

<400> SEQUENCE: 9
gctcaaccag tgaggcgtcc acgcctgccg ttcgcactgg atgcactggt tgagccaggc    60
c                                                                   61
```

```
<210> SEQ ID NO 10
<211> LENGTH: 61
<212> TYPE: DNA
<213> ORGANISM: Artificial Sequence
<220> FEATURE:
<223> OTHER INFORMATION: Primer

<400> SEQUENCE: 10
gctcaaccag tgaggcgtcc acgcctgccg ttcgcactgg atgcactggt tgagctcaca    60
t                                                                   61

<210> SEQ ID NO 11
<211> LENGTH: 61
<212> TYPE: DNA
<213> ORGANISM: Artificial Sequence
<220> FEATURE:
<223> OTHER INFORMATION: Primer

<400> SEQUENCE: 11
gctcaaccag tgaggcgtcc acgcctgccg ttcgcactgg atgcactggt tgagcctatc    60
t                                                                   61

<210> SEQ ID NO 12
<211> LENGTH: 61
<212> TYPE: DNA
<213> ORGANISM: Artificial Sequence
<220> FEATURE:
<223> OTHER INFORMATION: Primer

<400> SEQUENCE: 12
gctcaaccag tgaggcgtcc acgcctgccg ttcgcactgg atgcactggt tgagcgaaac    60
c                                                                   61

<210> SEQ ID NO 13
<211> LENGTH: 61
<212> TYPE: DNA
<213> ORGANISM: Artificial Sequence
<220> FEATURE:
<223> OTHER INFORMATION: Primer

<400> SEQUENCE: 13
gctcaaccag tgaggcgtcc acgcctgccg ttcgcactgg atgcactggt tgagctcagt    60
t                                                                   61

<210> SEQ ID NO 14
<211> LENGTH: 61
<212> TYPE: DNA
<213> ORGANISM: Artificial Sequence
<220> FEATURE:
<223> OTHER INFORMATION: Primer

<400> SEQUENCE: 14
gctcaaccag tgaggcgtcc acgcctgccg ttcgcactgg atgcactggt tgagctgggg    60
t                                                                   61

<210> SEQ ID NO 15
<211> LENGTH: 61
<212> TYPE: DNA
<213> ORGANISM: Artificial Sequence
<220> FEATURE:
<223> OTHER INFORMATION: Primer

<400> SEQUENCE: 15
```

-continued gctcaaccag tgaggcgtcc acgcctgccg ttcgcactgg atgcactggt tgagcgcttt    60
g                                                                     61

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ctgctgctat tgcacttgtc c                                               21

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
tgctgctatg gcttttcatt cct                                             23

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
ctgctgtaag gtgcatctag tgc                                             23

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gctgcagcta cattgtctgc tg                                              22

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tgctgctgtg caaatctatg caa                                             23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ctgctgctgt cagtttgtca aat                                             23

```
<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
ctgctgccag tgcaatagta ttgt                                              24

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
gctcaaccag tgaggcgtc                                                    19

<210> SEQ ID NO 24
<211> LENGTH: 21
<212> TYPE: DNA
<213> ORGANISM: Artificial Sequence
<220> FEATURE:
<223> OTHER INFORMATION: Probe

<400> SEQUENCE: 24
cgcctgccgt tcgcactgga t                                                 21

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
cacttgacca gagcagagag atga                                              24

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
tagagcgctt ctaactctgc agc                                               23

<210> SEQ ID NO 27
<211> LENGTH: 27
<212> TYPE: DNA
<213> ORGANISM: Artificial Sequence
<220> FEATURE:
<223> OTHER INFORMATION: Probe

<400> SEQUENCE: 27
tcctcaaaag attcataggg cttcagc                                           27
```

MARKER USED FOR DETECTION OF COLON CANCER, AND APPLICATION THEREOF

FIELD OF THE INVENTION

This application is a national stage application of PCT application PCT/CN2015/086956 filed on Aug. 14, 2015, which is hereby incorporated by reference herein in its entirety.

The present invention pertains to the field of biological and medical detection, and relates to markers for detection of colon cancer and also to application of said markers in detection of colon cancer, as well as an associated kit and detection method.

BACKGROUND OF THE INVENTION

Colon cancer is a common malignant tumor of digestive tract, and is in the second place of gastroenteric tumors. The predilection sites are rectum and the junction between rectum and sigmoid colon, which account for 60%. With changes of people's life style and dietary pattern, there is a tendency that morbidity and mortality of colorectal cancer rise year by year. The disease mostly occurs at the age of 40 afterward, and the ratio of male to female is 2:1. Currently, the method of early diagnosis of colorectal cancer comprises Fecal occult blood test (FOBT), Colonoscopy, stool DNA mutation detection and stool RNA-specific gene detection and so on, and Double-contrast barium enema (DCBE), etc. Colonoscopy is considered as a golden standard for diagnosing colorectal cancer. However, as it is an invasive examination, it requires intestinal tract preparation. During the examination, there are risks of occurring complications such as bleeding and perforation, so patient acceptance is not good and the cost is relatively high. Although fecal occult blood test is not an invasive detection, the examination results are susceptible to factors such as diets and the sensitivity and specificity of fecal occult blood test are not satisfactory as to screening of colorectal cancer.

Mature microRNAs (miRNAs) area class of single-stranded RNAs, each of which does not encode proteins and consists of 18 to 24 bases. Binding of a mature microRNA to corresponding mRNA results in degradation or silence of the mRNA, and then regulation of gene(s). Researches in recent years show that specific expression of miRNA is associated with development and progression of tumors, and some miRNAs can even play a role of anti-oncogenes or oncogenes. Cyclooxygenase (COX) is an important rate-limiting enzyme in the process of prostaglandin synthesis. COX2 is not expressed in a normal tissue, but may be expressed inducibly by the action of various stimulating factors. Thus, it is also called inductive early responsive gene which is closely related to development and progression of tumors. It is discovered in researches in recent years that COX2 is over-expressed in most head and neck tumors and that COX2 is also one of the biomarks for colon cancer. Therefore, if a corresponding colon cancer kit can be developed so that the kit can be applied in the field of scientific researches, the researches on colon cancer screening and transformation of scientific research achievements would be greatly accelerated, which necessarily plays a significant role in promoting diagnosis and treatment of colon cancer.

SUMMARY OF THE INVENTION

The inventors find out by research that over-expressions of miRNA-92a, miRNA-135b, miRNA-18a, miRNA-221, miRNA-19, miRNA-223 and miRNA-301a are associated with the development and progression of multiple human tumors (e.g., colon cancer), suggesting that detection for stool and serum miRNA-92a, miRNA-135b, miRNA-18a, miRNA-221, miRNa-19, miRNA-223 and miRNA-301a expressions can become one of the indicators for detecting tumors such as colon cancer.

The invention provides primers, probes and kits for detecting colon cancer (especially nucleic acids for detecting stool and serum miRNA-92a, miRNA-135b, miRNA-18a, miRNA-221, miRNA-19, miRNA-223, miRNA-301a and COX2) as well as detection methods.

The present invention comprises the following technical solutions:

1. A kit for detecting colon cancer, comprising a primer and/or a probe selecting from the group consisting of SEQ ID NOs: 9-27.

2. The kit according to Item 1, comprising one or more primers selecting from the group consisting of SEQ ID NOs: 9-15.

3. The kit according to Item 1 or 2, comprising the primer shown in SEQ ID NO: 23.

4. The kit according to any of Items 1 to 3, comprising the probe/probes shown in SEQ ID NO: 24 and/or 27.

5. The kit according to any of Items 1 to 4, comprising one or more primers selected from the group consisting of SEQ ID NOs: 16 to 22 and 25 to 26.

6. The kit according to any of Items 1 to 5, comprising one or more groups of primers and probes selecting from:
SEQ ID NOs: 9, 16, 23 and 24;
SEQ ID NOs: 10, 17, 23 and 24;
SEQ ID NOs: 11, 18, 23 and 24;
SEQ ID NOs: 12, 19, 23 and 24;
SEQ ID NOs: 13, 20, 23 and 24;
SEQ ID NOs: 14, 21, 23 and 24;
SEQ ID NOs: 15, 22, 23 and 24; and
SEQ ID NOs: 25 to 27.

7. The kit according to any of Items 1 to 6, wherein the probe(s) comprises/comprise a fluorescent label.

8. The kit according to Item 7, wherein 5' of the probe(s) is/are labeled with FAM, and 3' of the probe(s) is/are labeled with TAMRA.

9. Use of a reagent in preparing a kit for colon cancer detection, wherein the kit is used for determining one or more markers selected from the group consisting of miRNA-92a, miRNA-135b, miRNA-18a, miRNA-221, miRNA-19, miRNA-223, miRNA-301a and COX2, the reagent is preferably one or more primers and/or probes selected from the group consisting of SEQ ID NOs: 9 to 27.

10. A method for detecting colon cancer, comprising detecting in a sample a level of one or more markers selected from the group consisting of: miRNA-92a, miRNA-135b, miRNA-18a, miRNA-221, miRNA-19, miRNA-223, miRNA-301a and COX2, preferably using one or more primers and/or probes selected from SEQ ID NOs: 9 to 27 to detect the markers, wherein the sample is preferably a stool and/or serum sample.

The kit and method of the present invention employ a designed method (FIG. 1)—a hydrolysis probe method (TaqMan technology), which increases specificity by adding a gene-specific probe (generally of 20 to 30 bp) complementary to the template, apart from a pair of specific primers. Moreover, the probe may also be labeled with a fluorescent report group at its 5'-end and 3'-end respectively, to increase sensitivity. The primers, the probes, the kits and the methods of the present invention are applicable to detection and diagnosis for a colon cancer patient.

The primer and the probe for colon cancer detection are preferably:

(1) a reverse transcription primer, a probe and a detection primer for detection of miR-92a are illustrated as below:

miRNA-92a-RT (a reverse transcription primer):
(SEQ ID NO: 9)
5'-GCTCAACCAGTGAGGCGTCCACGCCTGCCGTTCGCACTGGATGCACT
GGTTGAGCCAGGCC-3';

miRNA-92a-F:
(SEQ ID NO: 16)
5'-CTGCTGCTATTGCACTTGTCC-3';

a universal reverse primer (miRNA-92a-R ):
(SEQ ID NO: 23)
5'-GCTCAACCAGTGAGGCGTC-3';

a universal probe (miRNA-92a-B):
(SEQ ID NO: 24)
5'-CGCCTGCCGTTCGCACTGGAT-3';

(2) a reverse transcription primer, a probe and a detection primer for detecting miRNA-135b are illustrated as below:

miRNA-135b-RT (a reverse transcription primer):
(SEQ ID NO: 10)
5'-GCTCAACCAGTGAGGCGTCCACGCCTGCCGTTCGCACTGGATGCACT
GGTTGAGCTCACAT-3';

miRNA-135b-F:
(SEQ ID NO: 17)
5'-TGCTGCTATGGCTTTTCATTCCT-3';

a universal reverse primer (miRNA-135b-R):
(SEQ ID NO: 23)
5'-GCTCAACCAGTGAGGCGTC-3';

a universal probe (miRNA-135b-B):
(SEQ ID NO: 24)
5'-CGCCTGCCGTTCGCACTGGAT-3';

(3) a reverse transcription primer, a probe and a detection primer for detection of miRNA-18a are illustrated as below;

miRNA-18a-RT (a reverse transcription primer):
(SEQ ID NO: 11)
5'-GCTCAACCAGTGAGGCGTCCACGCCTGCCGTTCGCACTGGATGCACT
GGTTGAGCCTATCT-3';

miRNA-18a-F (a forward primer used for detection):
(SEQ ID NO: 18)
5'-CTGCTGTAAGGTGCATCTAGTGC-3';

a universal reverse primer (miRNA-18a-R):
(SEQ ID NO: 23)
5'-GCTCAACCAGTGAGGCGTC-3';

a universal probe (miRNA-18a-B):
(SEQ ID NO: 24)
5'-CGCCTGCCGTTCGCACTGGAT-3';

(4) a reverse transcription primer, a probe and a detection primer used for detection of miR-221 are illustrated as below:

miR-221-RT (a reverse transcription primer):
(SEQ ID NO: 12)
5'-GCTCAACCAGTGAGGCGTCCACGCCTGCCGTTCGCACTGGATGCACT
GGTTGAGCGAAACC-3';

miR-221-F (a forward primer):
(SEQ ID NO: 19)
5'-GCTGCAGCTACATTGTCTGCTG-3';

a universal reverse primer (miR-221-R):
(SEQ ID NO: 23)
5'-GCTCAACCAGTGAGGCGTC-3';

a universal probe (miR-221-B):
(SEQ ID NO: 24)
5'-CGCCTGCCGTTCGCACTGGAT-3';

(5) a reverse transcription primer, a probe and a detection primer used for detecting miRNA-19 are illustrated as below:

miRNA-19-RT (a reverse transcription primer):
(SEQ ID NO: 13)
5'-GCTCAACCAGTGAGGCGTCCACGCCTGCCGTTCGCACTGGATGCACT
GGTTGAGCTCAGTT-3';

miRNA-19-F (a forward primer):
(SEQ ID NO: 20)
5'-TGCTGCTGTGCAAATCTATGCAA-3';

a universal reverse primer (miRNA-19-R):
(SEQ ID NO: 23)
5'-GCTCAACCAGTGAGGCGTC-3';

a universal probe (miRNA-19-B):
(SEQ ID NO: 24)
5'-CGCCTGCCGTTCGCACTGGAT-3';

(6) a reverse transcription primer, a probe and a detection primer used for detection of miRNA-223 are illustrated as below:

miRNA-223-RT (a reverse transcription primer):
(SEQ ID NO: 14)
5'-GCTCAACCAGTGAGGCGTCCACGCCTGCCGTTCGCACTGGATGCACT
GGTTGAGCTGGGGT-3';

miRNA-223-F (a forward primer):
(SEQ ID NO: 21)
5'-CTGCTGCTGTCAGTTTGTCAAAT-3';

a universal reverse primer (miRNA-223-R):
(SEQ ID NO: 23)
5'-GCTCAACCAGTGAGGCGTC-3';

a universal probe (miRNA-223-B):
(SEQ ID NO: 24)
5'-CGCCTGCCGTTCGCACTGGAT-3';

(7) a reverse transcription primer, a probe and a detection primer used for detection of miRNA-301a are illustrated as below:

miRNA-301a-RT (a reverse transcription primer):
(SEQ ID NO: 15)
5'-GCTCAACCAGTGAGGCGTCCACGCCTGCCGTTCGCACTGGATGCACT
GGTTGAGCGCTTTG-3';

miRNA-301a-F (a forward primer):
(SEQ ID NO: 22)
5'-CTGCTGCCAGTGCAATAGTATTGT-3';

a universal reverse primer (miRNA-301a-R):
(SEQ ID NO: 23)
5'-GCTCAACCAGTGAGGCGTC-3';

-continued a universal probe (miRNA-301a-B):
(SEQ ID NO: 24)
5'-CGCCTGCCGTTCGCACTGGAT-3'T;

(8) a primer and a probe used for detection of COX2 are illustrated as below:

COX2-B (a probe):
(SEQ ID NO: 27)
5'-TCCTCAAAAGATTCATAGGGCTTCAGC-3';

COX2-F (a forward primer):
(SEQ ID NO: 25)
5'-CACTTGACCAGAGCAGAGAGATGA-3';

COX2-R (a reverse primer):
(SEQ ID NO: 26)
5'-TAGAGCGCTTCTAACTCTGCAGC-3'.

The sequences of the primers of microRNAs are designed based on the nucleotide sequences of miRNA-92a (MI-MAT0000092), miRNA-135b (MIMAT0000758), miRNA-18a (MIMAT0000072), miRNA-221 (MIMAT0000278), miRNA-19 (MIMAT0000073), miRNA-223 (MI-MAT0000280), miRNA-301a (MIMAT0000688) reported in microRNA database (http://www.mirbase.org) and the COX2 sequence (JN793538) in the GeneBank database as templates. Table 1 lists the nucleotide sequences of the miRNAs.

TABLE 1

| miRNA Name | Sequences | (Accession No.) | SEQ ID NO: |
|---|---|---|---|
| hsa-miR-92 | uauugcacuuguccggccug | MIMAT0000092 | 1 |
| miRNA-135b | uauggcuuuucauuccuauguga | MIMAT0000758 | 2 |
| miRNA-18a | uaaggugcaucuagugcagauag | MIMAT0000072 | 3 |
| miRNA-221 | agcuacauugucugcuggguuuc | MIMAT0000278 | 4 |
| hsa-miR-19a | ugugcaaaucuaugcaaaacuga | MIMAT0000073 | 5 |
| hsa-miR-223 | ugucaguuugucaaauacccca | MIMAT0000280 | 6 |
| hsa-miR-301a | cagugcaauaguauugucaaagc | MIMAT0000688 | 7 |

COX2 Sequence (Accession No.: JN793538) as below:

(SEQ ID NO: 8)
CACTTGACCAGAGCAGAGAGATGAAATACCAGTCTTTTAATGAGTATCGC

AAACGTTTTCTGCTGAAGCCCTATGAATCTTTTGAGGAACTTACAGGAGA

GAAGGAAATGGCTGCAGAGTTAGAAGCGCTCTA.

The samples that can be detected by the kit in the disclosure are stools, throat swabs, cloaca swabs, tissue samples, serum or plasma, blister fluids, cerebro-spinal fluids or samples of a virus separation culture derived from suspected patients (e.g., persons) of colon cancer, preferably stool, and then preferably serum.

The embodiments disclosed therein can readily realize accurate diagnosis of colon cancer by detection of a small amount of miRNA(s) and COX2, and offers possibilities of producing accurate, efficient and economical detection products. The established colon cancer detection model can satisfactorily distinguish between individuals with colon cancer and healthy ones, and has important clinical and practical significance to timely treatment and prevention for colon cancer patients.

As known by persons skilled in the art, proper changes and modifications can be made to primer sequences and probe sequences disclosed therein based on the sequences of associated markers (the miRNAs and COX2), and these modified primer sequences and probe sequences can still be used for detection of the markers. The present invention also includes these equivalent embodiments.

BRIEF DESCRIPTION OF THE DRAWINGS

FIG. 1 is a schematic diagram of the probe detection method.
FIG. 2 shows the detection limit of miRNA-19.
FIG. 3 shows the detection limit of miRNA-135b.
FIG. 4 shows the detection limit of miRNA-18a.
FIG. 5 shows the detection limit of miRNA-221.
FIG. 6 shows the detection limit of miRNA-92a.
FIG. 7 shows the detection limit of miRNA-223.
FIG. 8 shows the detection limit of miRNA-301a.
FIG. 9 shows the detection limit of COX2.
FIG. 10 shows the expression level of miRNA-19.
FIG. 11 shows the expression level of miR-92a.
FIG. 12 shows the expression level of miRNA-135b.
FIG. 13 shows the expression level of miRNA-18a.
FIG. 14 shows the expression level of miR-221.
FIG. 15 shows the expression level of miR-223.
FIG. 16 shows the expression level of miR-301a.
FIG. 17 shows the expression level of COX2.

DETAILED DESCRIPTION OF THE EMBODIMENTS

The invention will be described hereinafter by reference to specific examples. The following experimental methods in Examples are all routine methods if not specified otherwise. The medicinal materials, the reagent materials and the like used in the following Examples are all products available in the market if not specified otherwise.

Example 1 Primer and Probe Design and Establishment and Optimization of Reaction System 1. Primer and Probe Design:

The primer and probe sequences are designed based on the sequences of corresponding miRNAs and Cox2. Specific sequences are shown as in Table 2.

TABLE 2

| Primer Names | Sequences |
| --- | --- |
| miRNA-92a-RT | 5'-GCTCAACCAGTGAGGCGTCCACGCCTGCCG TTCGCACTGGATGCACTGGTTGAGCCAGGCC-3' (SEQ ID NO: 9) |
| miRNA-135b-RT | 5'-GCTCAACCAGTGAGGCGTCCACGCCTGCCG TTCGCACTGGATGCACTGGTTGAGCTCACAT-3' (SEQ ID NO: 10) |
| miRNA-18a-RT | 5'-GCTCAACCAGTGAGGCGTCCACGCCTGCCG TTCGCACTGGATGCACTGGTTGAGCCTATCT-3' (SEQ ID NO: 11) |
| miRNA-221-RT | 5'-GCTCAACCAGTGAGGCGTCCACGCCTGCCG TTCGCACTGGATGCACTGGTTGAGCGAAACC-3' (SEQ ID NO: 12) |
| miRNA-19-RT | 5'-GCTCAACCAGTGAGGCGTCCACGCCTGCCG TTCGCACTGGATGCACTGGTTGAGCTCAGTT-3' (SEQ ID NO: 13) |
| miRNA-223-RT | 5'-GCTCAACCAGTGAGGCGTCCACGCCTGCCG TTCGCACTGGATGCACTGGTTGAGCTGGGGT-3' (SEQ ID NO: 14) |
| miRNA-301a-RT | 5'-GCTCAACCAGTGAGGCGTCCACGCCTGCCG TTCGCACTGGATGCACTGGTTGAGCGCTTTG-3' (SEQ ID NO: 15) |
| miRNA-92a-F | 5'-CTGCTGCTATTGCACTTGTCC-3' (SEQ ID NO: 16) |
| miRNA-135b-F | 5'-TGCTGCTATGGCTTTTCATTCCT-3' (SEQ ID NO: 17) |
| miRNA-18a-F | 5'-CTGCTGTAAGGTGCATCTAGTGC-3' (SEQ ID NO: 18) |
| miR-221-F | 5'-GCTGCAGCTACATTGTCTGCTG-3' (SEQ ID NO: 19) |
| miRNA-19-F | 5'-TGCTGCTGTGCAAATCTATGCAA-3' (SEQ ID NO: 20) |
| miRNA-223-F | 5'-CTGCTGCTGTCAGTTTGTCAAAT-3' (SEQ ID NO: 21) |
| miRNA-301a-F | 5'-CTGCTGCCAGTGCAATAGTATTGT-3' (SEQ ID NO: 22) |
| a universal reverse primer of the miRNAs (used for miRNA-92a, miRNA-135b, miRNA-18a, miRNA-221, miRNA-19, miRNA-223 and miRNA-301a) | 5'-GCTCAACCAGTGAGGCGTC-3' (SEQ ID NO: 23) |
| a universal probe of the miRNAs (used for miRNA-92a, miRNA-135b, miRNA-18a, miRNA-221, miRNA-19, miRNA-223 and miRNA-301a) | 5'-CGCCTGCCGTTCGCACTGGAT-3' (SEQ ID NO: 24) |
| COX2-F | 5'-CACTTGACCAGAGCAGAGAGATGA-3' (SEQ ID NO: 25) |
| COX2-R | 5'-TAGAGCGCTTCTAACTCTGCAGC-3' (SEQ ID NO: 26) |
| COX2-B | 5'-TCCTCAAAAGATTCATAGGGCTTCAGC-3' (SEQ ID NO: 27) |

Note:
5' of the probe is labeled with FAM, and 3' of the probe is labeled with TAMRA.

2. Establishment and Optimization of the Reaction System of a Colon Cancer PCR Diagnostic kit 2.1 Sample Collection Samples were collected from people diagnosed of chronic colitis, ulcerative colitis, intestinal polypus, adenomatous polypus, colorectal cancer at different phases and the like via endoscopy to detect the expression levels of miR-92a, miRNA-135b, miRNA-18a, miRNA-221, miRNA-19, miRNA-223, miRNA-301a and COX2.

2.2 Extraction of RNA

The RNA extraction liquid is purchased from a renowned molecular biological company, Molecular Research Center (MRC), US.

1) The sample is taken out from −80° C. and then placed on ice (clinical samples were collected when placed on ice, split into centrifugal tubes at about 0.5 g/2 ml and then stored at −80° C.);
2) 1 ml of a TRIzol LS Reagent is added and vortexed so that the sample is uniformly distributed, and then placed still at room temperature for 5 minutes;
3) 200 µl of chloroform is added, vortexed, placed still at room temperature for one to two minutes, and centrifuged at 4° C. for 15 min at 12000 rcf;
4) The upper homogeneous aqueous phase (400 µl) is transferred into a new centrifugal tube, added with 1.5 volume of 100% ethanol (600 µl) and mixed thoroughly by pipetting slowly (without vortexing);
5) A RNeasy adsorption column is loaded with 700 µl at a time, and spun at >12000 rcf/8000 g at 4° C. for 30 seconds, and then the elute is discarded;
6) The purification column is spun at a maximum speed for one minute at 4° C.;
7) 30 µl of RNase-free water is added, and then centrifugation is carried out at >12000 rcf/8000 g at 4° C. for one minute to elute total RNA;
8) More 30 µl of RNase-free water is added and centrifugation is carried out at >12000 rcf/8000 g at 4° C. for one minute for second elution (RNAs can be collected in the same tube with the first eluted RNAs), and then placed on ice;
9) The concentration and purity of the resultant total RNA are determined.

The RNAs extracted by the method provided above are reverse transcribed into cDNAs. The reverse transcription system of the RNAs is as follows (Table 3):

TABLE 3

| Components | Final Concentration |
| --- | --- |
| 20× reverse transcription buffer | 1× |
| concentration of $Mg^{2+}$ | 5.0 mmol/L |
| dNTPs (including dUTP) | 0.3 mmol/L |
| reverse transcriptase | 5 U |
| reverse transcription primer | 0.15 µmol/L |
| template | 2 µg |
| water added to | 25 µL |

The conditions of RNA reverse transcription were: 16° C. 30 minutes; 42° C. 35 minutes; 80° C. 5 minutes; cDNAs were preserved at 4° C. for subsequent PCR amplification.

2.3 Optimization of PCR Primer Concentration

In the reaction system, determination was carried out after primers of miRNA-92a, miRNA-135b, miRNA-18a, miRNA-221, miRNA-19, miRNA-223, miRNA-301a and COX2 were serially fold diluted from 0.1 µmol/L to 0.6 µmol/L, respectively. By analysis and comparison of the experimental results, it can be determined that the optimal primer final concentrations of miRNA-92a, miRNA-135b, miRNA-18a, miRNA-221, miRNA-19, miRNA-223, miRNA-301a and COX2 are 0.20 µmol/L, 0.20 µmol/L, 0.20 µmol/L, 0.20 µmol/L, 0.20 µmol/L, 0.20 µmol/L, 0.20 µmol/L, 0.25 µmol/L, respectively.

2.4 Optimization of Magnesium Ion Concentration

On the premise of unchanging other conditions in the reaction system, the concentration of $MgCl_2$ was gradually increased from 2.5 mmol/L to 5.5 mmol/L by 0.5 mmol/L, and it was determined after several repeated experiments that 3.0 mmol/L is the concentration of Magnesium ions in the reaction system of the kit.

2.5 Optimization of the Amount of Taq DNA Polymerase (Taq Enzyme)

3U was selected as the amount of Taq enzyme in the reaction system of the kit by comparing the optimized experimental results of the Taq enzyme amount (by unit).

2.6 Optimization of dNTP Concentration

It was determined by comprehensive evaluation that 0.25 mmol/L is the amount of dNTPs used in the reaction system of the kit after using different concentrations of dNTPs for detection.

2.7 Optimization of Probe Concentration

In the reaction system, determination was carried out after the probes were serially fold diluted from 0.05 µmol/L to 0.2 µmol/L, respectively. By analysis and comparison of the experimental results, it can be determined that the optimal probe final concentrations of miRNA-92a, miRNA-135b, miRNA-18a, miRNA-221, miRNA-19, miRNA-223, miRNA-301a and COX2 are 0.10 µmol/L, 0.10 µmol/L, 0.10 µmol/L, 0.10 µmol/L, 0.10 µmol/L, 0.10 µmol/L, 0.1 µmol/L, 0.15 µmol/L, respectively.

The reaction system was established using the abovementioned primers and probes, and it is finally determined that the fluorescent PCR reaction system employed is a 25 µl system. Reference of the required components and corresponding concentrations can be made to Table 3.

TABLE 4

Optimized PCR Reaction System

| Components | Final Concentrations |
| --- | --- |
| 20×PCR Reaction Buffer | 1× |
| Concentration of $Mg^{2+}$ | 3.0 mmol/L |
| dNTPs (including dUTP) | 0.25 mmol/L |
| Taq enzyme | 3 U |
| Primers of miRNA-92a, miRNA-135b, miRNA-18a, miRNA-221, miRNA-19, miRNA-223 and miRNA-301a | 0.20 µmol/L |
| Probes of miRNA-92a, miRNA-135b, miRNA-18a, miRNA-221, miRNA-19, miRNA-223 andmiRNA-301a | 0.10 µmol/L |
| COX2 Primer | 0.25 µmol/L |
| COX2-B Probe | 0.15 mol/L |
| Template | 5 µl |
| Water added to | 25 µl |

Note:
a. Each of the reagents should be proportionally adjusted when the volume of the fluorescent PCR reaction is different.
b. The reaction parameters should be properly adjusted owing to a different apparatus is used.

3. Selection of the Apparatus Detection Channel:

During the fluorescent PCR reaction, the collection of the fluorescent signals from the reaction tubes in the apparatus as used should be set, and the selected fluorescent detection channel is consistent with the fluorescent reporter group(s)

labeling corresponding probe. The specific method varies with the apparatus, and reference should be made to the description of the apparatus.

4. The Conditions of PCR were Selected as Below:

Conditions of PCR amplification: 95° C. for 3 minutes, one cycle; 95° C. for 5 seconds, 60° C. for 45 seconds, 40 cycles.

Example 2 Determining the Detection Limits of miRNA-92a, miRNA-135b, miRNA-18a, miRNA-221, miRNA-19, miRNA-223, miRNA-301a and COX2 by Detecting the Copy Numbers Thereof The positive samples of miRNA-92a, miRNA-135b, miRNA-18a, miRNA-221, miRNA-19, miRNA-223, miRNA-301a and COX2 as provided by Chinese University of Hong Kong at concentrations of $10^6$ copies/ml were 10-fold diluted to $10^5$ copies/ml, $10^4$ copies/ml, $10^3$ copies/ml, $2.5 \times 10^2$ copies/ml and $10^2$ copies/ml. Fluorescent PCR detection was carried out using the designed primers and probes and the established reaction system, apparatus and amplification conditions in Example 1.

Results indicate that the CT value is 32 at $2.5 \times 10^3$ copies/ml, and other individual indicators also comply with the detection requirements. Therefore, the detection sensitivity is enhanced in the present invention by optimizing the primers and the probes, and the detection limit thereof can reach $2.5 \times 10^3$ copies/ml. Results are shown in FIGS. 2 to 6.

Example 3 Determining the Expressions of miRNA-92a, miRNA-135b, miRNA-18a, miRNA-221, miRNA-19, miRNA-223, miRNA-301a and COX2 in the Samples and the Specificity Thereof People diagnosed of chronic colitis, ulcerative colitis, intestinal polypus, adenomatous polypus, colorectal cancer at different phases and the like via complete colonoscopy in Tianjin People's Hospital are collected. Fifty-five cases of colorectal cancer, 10 cases of adenoma, and 15 cases of normal people were selected to collect their stool samples to determine expression levels and specificity of miR-92a, miRNA-135b, miRNA-18a, miRNA-221, miRNA-19, miRNA-223, miRNA-301a and COX2.

It can be determined based on the results that:

The expressions of miR-92a, miRNA-135b, miRNA-18a, miRNA-221, miRNA-19, miRNA-223, miRNA-301a, and COX2 in stools of 55 cases of patients with colorectal cancer, 10 cases of patients with adenoma and 15 cases of healthy controls are shown in FIGS. 10 to 17. Data processing is performed on the expression levels of miR-92a, miRNA-135b, miRNA-18a, miRNA-221, miRNA-19, miRNA-223, miRNA-301a and COX2 in the stools of patients with colorectal cancer, patients with adenoma and healthy controls. The results are indicated in Table 5. It is concluded by statistical analysis of the results using SPSS13.0 that the expression levels of miR-92a, miRNA-135b, miRNA-18a, miRNA-221, miRNA-19, miRNA-223, miRNA-301a, COX2 in the stools of patients with colon cancer are significantly higher than those of patients with adenoma and healthy controls, and the differences are statistically significant ($P<0.01$). Reference can be made to FIGS. 10 to 17. The critical values that distinguish the copy numbers of the expressions of miR-92a, miRNA-135b, miRNA-18a, miRNA-221, miRNA-19, miRNA-223, miRNA-301a and COX2 in the stools between patients with colon cancer and patients not diagnosed of colon cancer are 1360, 66, 1255, 156, 425, 9000, 50 and 925, respectively (see Table 5).

The comprehensive results indicate that the expression levels of miR-92a, miRNA-135b, miRNA-18a, miRNA-221, miRNA-19, miRNA-223, miRNA-301a and COX2 in the stools can serve as the indicators of diagnosis of colon cancer, and have important diagnostic significance.

TABLE 5

| miRNA | Significant difference between patients with colon cancer and normal people | Critical values (copies/ng RNA) | Specificity |
|---|---|---|---|
| miRNA-19 | P < 0.001 | 1360 | 96% |
| miRNA-135b | P < 0.001 | 66 | 88% |
| miRNA-18a | P < 0.005 | 1255 | 96% |
| miRNA-221 | P < 0.003 | 156 | 92% |
| miRNA-92a | P < 0.001 | 425 | 84% |
| miRNA-223 | P < 0.001 | 9000 | 96% |
| miRNA-301a | P < 0.001 | 50 | 100% |
| COX2 | P < 0.001 | 925 | 92% |

The invention claimed is:

1. A kit for detecting colon cancer, comprising a reverse transcription primer which is SEQ ID NO: 9, a first primer which is SEQ ID NO: 16, a second primer which is SEQ ID NO: 23, and a probe which is SEQ ID NO: 24.

2. The kit according to claim 1, comprising one or more additional primers each which is SEQ ID NO: 10, SEQ ID NO: 11, SEQ ID NO: 12, SEQ ID NO: 13, SEQ ID NO: 14, or SEQ ID NO: 15.

3. The kit according to claim 1, comprising an additional probe which is SEQ ID NO: 27.

4. The kit according to claim 1, comprising one or more additional primers each which is SEQ ID NO: 17, SEQ ID NO: 18, SEQ ID NO: 19, SEQ ID NO: 20, SEQ ID NO: 21, SEQ ID NO: 22, SEQ ID NO: 25, or SEQ ID NO: 26.

5. The kit according to claim 1, comprising one or more sets of primers and probes, wherein the one or more sets are selected from a group consisting of:
- a set of primers and probe each which is SEQ ID NO: 10, SEQ ID NO: 17, SEQ ID NO: 23, or SEQ ID NO: 24;
- a set of primers and probe each which is SEQ ID NO: 11, SEQ ID NO: 18, SEQ ID NO: 23, or SEQ ID NO: 24;
- a set of primers and probe each which is SEQ ID NO: 12, SEQ ID NO: 19, SEQ ID NO: 23, or SEQ ID NO: 24;
- a set of primers and probe each which is SEQ ID NO: 13, SEQ ID NO: 20, SEQ ID NO: 23, or SEQ ID NO: 24;
- a set of primers and probe each which is SEQ ID NO: 14, SEQ ID NO: 21, SEQ ID NO: 23, or SEQ ID NO: 24;
- a set of primers and probe each which is SEQ ID NO: 15, SEQ ID NO: 22, SEQ ID NO: 23, or SEQ ID NO: 24; and
- a set of primers and probe each which is SEQ ID NO: 25, SEQ ID NO: 26, or SEQ ID NO: 27.

6. The kit according to claim 1, wherein the probe comprises a fluorescent label.

7. The kit according to claim 6, wherein 5' of the probe is labeled with FAM, and 3' of the probe is labeled with TAMRA.

8. The kit according to claim 2, comprising an additional probe which is SEQ ID NO: 27.

9. The kit according to claim 4, wherein the probe comprises a fluorescent label.

10. The kit according to claim 9, wherein 5' of the probe is labeled with FAM, and 3' of the probe is labeled with TAMRA.

11. The kit according to claim 5, wherein the probe comprises a fluorescent label.

12. The kit according to claim 11, wherein 5' of the probe is labeled with FAM, and 3' of the probe is labeled with TAMRA.

13. The kit according to claim 1, further comprising an additional primer or an additional probe, wherein the additional primer or the additional probe which is SEQ ID NO: 10, SEQ ID NO: 11, SEQ ID NO: 12, SEQ ID NO: 13, SEQ ID NO: 14, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 25, SEQ ID NO: 26, or SEQ ID NO: 27.

* * * * *